(12) United States Patent
Rosch et al.

(10) Patent No.: US 9,265,819 B2
(45) Date of Patent: Feb. 23, 2016

(54) **LIVE, ATTENUATED *STREPTOCOCCUS PNEUMONIAE* STRAIN AND VACCINE FOR PROTECTION AGAINST PNEUMOCOCCAL DISEASE**

(71) Applicant: St. Jude Children's Research Hospital, Memphis, TN (US)

(72) Inventors: Jason W. Rosch, Memphis, TN (US); Elaine I. Tuomanen, Germantown, TN (US); Jonathan A. McCullers, Memphis, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 0 days.

(21) Appl. No.: 14/345,988

(22) PCT Filed: Sep. 19, 2012

(86) PCT No.: PCT/US2012/055986
§ 371 (c)(1),
(2) Date: Mar. 20, 2014

(87) PCT Pub. No.: WO2013/043643
PCT Pub. Date: Mar. 28, 2013

(65) Prior Publication Data
US 2014/0314812 A1  Oct. 23, 2014

Related U.S. Application Data

(60) Provisional application No. 61/537,290, filed on Sep. 21, 2011.

(51) Int. Cl.
*A61K 39/09* (2006.01)
*A61K 39/00* (2006.01)

(52) U.S. Cl.
CPC ......... *A61K 39/092* (2013.01); *A61K 2039/522* (2013.01); *A61K 2039/543* (2013.01)

(58) Field of Classification Search
CPC ..... A61K 39/09; A61K 39/522; A61K 39/00; A61K 39/092; A61K 2039/522
USPC .......................... 435/253.4, 252.3; 424/244.1
See application file for complete search history.

(56) References Cited

U.S. PATENT DOCUMENTS

| | | | | |
|---|---|---|---|---|
| 5,958,730 A * | 9/1999 | Skatrud et al. | ................ | 435/69.1 |
| 6,072,032 A * | 6/2000 | Black et al. | .................... | 530/350 |
| 6,159,949 A * | 12/2000 | Black et al. | ................. | 514/44 R |
| 6,692,951 B2 * | 2/2004 | Quax et al. | ................ | 435/252.31 |
| 7,381,814 B1 * | 6/2008 | Doucette-Stamm et al. | | 536/23.7 |
| 2002/0058790 A1 * | 5/2002 | Black et al. | .................... | 530/350 |
| 2002/0068068 A1 * | 6/2002 | Mahan et al. | ............. | 424/200.1 |
| 2002/0103104 A1 * | 8/2002 | Cheever | ................ | C07K 14/31 514/1 |
| 2005/0287169 A1 * | 12/2005 | Belitsky | ..................... | 424/200.1 |
| 2006/0182685 A1 * | 8/2006 | Bishai | .............. | A61K 47/48976 424/9.2 |
| 2006/0281110 A1 * | 12/2006 | Britton et al. | ...................... | 435/6 |
| 2007/0184443 A1 * | 8/2007 | Covacci | ............................. | 435/6 |
| 2009/0252756 A1 * | 10/2009 | Mizrachi-Nebenzahl | . | 424/190.1 |
| 2009/0297549 A1 * | 12/2009 | Tettelin et al. | ............. | 424/190.1 |
| 2009/0324651 A1 * | 12/2009 | Old et al. | .................... | 424/277.1 |
| 2010/0184137 A1 * | 7/2010 | Van Kimmenade et al. | | 435/69.1 |
| 2012/0321687 A1 * | 12/2012 | Hughes et al. | ................ | 424/405 |
| 2014/0127816 A1 * | 5/2014 | Hanson et al. | ................ | 435/471 |
| 2014/0154286 A1 * | 6/2014 | Malley | ................... | C07K 14/31 424/190.1 |

FOREIGN PATENT DOCUMENTS

EP       0906955      * 4/1999 ............. C12N 15/31

OTHER PUBLICATIONS

Pinto, E et al, European Society of Clinical Microbiology and Infectious Diseases, 17th European Congress of Clinical Microbiology and Infectious Diseases ICC, Munich, Germany, Mar. 31-Apr. 4, 2007, The Importance of signal recognition particle for viability of *Streptococcus pneumoniae*, Abstract No. 1733_919, one page.*
Hasona, Adnan et al, Streptococcal viability and diministhed stress tolerance in mutants lacking the signal recognition particle pathway or YidC2, PNAS, pp. 17466-17471, Nov. 29, 2005, vol. 102(48).*
Crowley, Paula J. et al, FEMS Microbiology Letters, vol. 234, 2004, pp. 315-324, An ffh mutant of *Streptococcus mutans* is viable and able to physiologically adapt to low pH in continuous culture.*
Lam, Vinh Q. et al, Journal of Cell Biology, vol. 190(4), pp. 623-635, Lipid activation of the signal recognition particle receptor provides spatial coordination of protein targeting.*
Rosch, Jason W et al, EMBO Molecular Medicine, A live attenuated pneumococcal vaccine elicits CD4+ T-cell dependent class switching and provides serotype independent protection against acute otitis media, vol. 6(1), pp. 141-154, 2014.*
Bartilson, Magdalena et al, Molecular Microbiology, 2001, vol. 39(1), pp. 126-135.*
Peterson, Scott N. et al, Molecular Microbiology, 2004, vol. 51(4), pp. 1051-1070, Identification of competence pheromone responsive genes in *Streptococcus pneumoniae* by use of DNA microarrays.*
Egea, Pascal F. et al, Substrate twinning activates the signal recognition particle and its receptor, Nature, vol. 427, Jan. 15, 2004, pp. 215-221.*
Shan, Shu-on et al, Molecular Crosstalk between Nucleotide Specificity Determinant of the SRP GTPase and the SRP Receptor, Biochemistry, 2005, vol. 44, pp. 6214-6222.*
Hasona, Adnan et al, Streptococcal viability and diminished stress tolerance in mutants lacking the signal recognition particle pathway or YidC2, PNAS, vol. 102(48), pp. 17466-17471, Nov. 29, 2005.*

(Continued)

*Primary Examiner* — Albert Navarro
*Assistant Examiner* — Ginny Portner
(74) *Attorney, Agent, or Firm* — Licata & Tyrrell P.C.

(57) ABSTRACT

The present invention is an attenuated mutant strain of *Streptococcus pneumonia* that has a mutation in the FtsY gene. Vaccines, kits and methods for protecting a subject against *Streptococcus pneumonia* disease or colonization using the attenuated mutant strain are also provided.

6 Claims, No Drawings

(56) References Cited

OTHER PUBLICATIONS

Koch, H.G. et al, Rev. Physiol. Biochem. Pharmacol. 2003, vol. 146, pges 55-94, Signal recognition particle dependent protein targeting, universal to all kingdoms of life.*

Block et al. "Community-Wide Vaccination with the Heptavalent Pneumococcal Conjugate Significantly Alters the Microbiology of Acute Otitis Media" The Pediatric Infectious Disease Journal 2004 23(9):829-833.

Coker et al. "Diagnosis, Microbial Epidemiology, and Antibiotic Treatment of Acute Otitis Media in Children" JAMA 2010 304(19):2161-2169.

Daly et al. "Epidemiology of Otitis Media Onset by Six Months of Age" Pediatrics 1999 103:1158-1166.

Eskola et al. "Efficacy of a Pneumococcal Conjugate Vaccine Against Acute Otitis Media" New England Journal of Medicine 2001 344(6):403-409.

McCaig et al. "Trends in Antimicrobial Prescribing Rates for Children and Adolescents" JAMA 2002 287(23):3096-3102.

Roche et al. "Live Attenuated *Streptococcus pneumoniae* Strains Induce Serotype-Independent Mucosal and Systemic Protection in Mice" Infection and Immunity 2007 75(5):2469-2475.

Sabirov, A. and Metzger, D.W. "Intranasal Vaccination of Neonatal Mice with Polysaccharide Conjugate Vaccine for Protection Against Pneumococcal Otitis Media" Vaccine 2006 24:5584-5592.

International Preliminary Report on Patentability from PCT/US2012/055986, Apr. 3, 2014.

International Search Report from PCT/US2012/055986, Nov. 20, 2012.

* cited by examiner

LIVE, ATTENUATED *STREPTOCOCCUS PNEUMONIAE* STRAIN AND VACCINE FOR PROTECTION AGAINST PNEUMOCOCCAL DISEASE

INTRODUCTION

This application is a U.S. National Stage Application of PCT/US2012/055986 filed Sep. 19, 2012 and claims the benefit of priority of U.S. Provisional Application Nos. 61/537,290, filed Sep. 21, 2011, the contents of each of which are incorporated herein by reference in their entirety.

This invention was made with government support under grant number 1RC1D010566-01 awarded by the National Institute on Deafness and other Communication Disorders.

BACKGROUND OF THE INVENTION

Acute otitis media (AOM) is one of the most common infectious diseases of children and the most common infection for which antibiotics are prescribed in the United States (Daly, et al. (1999) *Pediatrics* 103:1158-1166; McCaig, et al. (2002) *JAMA* 287:3096-3102). *Streptococcus pneumoniae* remains one of the most prevalent causes of AOM even after the advent of the heptavalent conjugate vaccine (Coker, et al. (2010) *JAMA* 304:2161-2169). Vaccination is viewed as a critical method of prevention but has been largely unsuccessful in changing the incidence of AOM. The 23-valent polysaccharide vaccine does not elicit antibodies in children under age 2 and is not protective against AOM in any age group. The heptavalent conjugate pneumococcal vaccine (PREVNAR) is highly protective against invasive disease from birth but again fails to significantly impact the rate of AOM (Eskola, et al. (2001) *N. Engl. J. Med.* 344:403-409). The high effect of AOM on children's medical care and the absence of effective preventive intervention indicates that new vaccine concepts are urgently needed.

Otitis media caused by *S. pneumoniae* is a significant medical burden in children. Although the advent of the pneumococcal polyvalent conjugate vaccine PREVNAR (PCV7) has decreased the overall burden of pneumococcal disease, the suboptimal mucosal immune response elicited by this vaccine does not provide effective protection. Even with vaccination, AOM is the leading cause of pediatric physician visits and is responsible for a majority of the antibiotics prescribed to young children (Daly, et al. (1999) supra; McCaig, et al. (2002) supra). Furthermore, as is the risk with all polysaccharide capsule-based vaccines, the risk of an increasing burden of non-vaccine serotypes remains problematic and quickly emerges (Block, et al. (2004) *Pediatr. Infect. Dis. J.* 23:829-833; Eskola, et al. (2001) supra). This underscores the importance of development of new vaccination strategies that would confer cross-serotype protection as well as a greater understanding of host mucosal immunity.

Studies in animal models have demonstrated that the intranasal route of vaccination is particularly effective at inducing immune responses in the nasal passage and middle ear for protection against AOM (Sabirov & Metzger (2006) *Vaccine* 24:5584-5592). Further, application of live, attenuated *S. pneumoniae* mediates a potent, serotype-independent mucosal and humoral immune response that was protective against subsequent invasive challenge (Roche, et al. (2007) *Infect. Immun.* 75:2469-2475). These studies suggest that a vaccine effective against AOM should optimally be live, attenuated, and be given intranasally. However, these vaccines may not be optimal because they were generated by deleting several important, highly immunogenic virulence factors, which are currently being developed as components of protein-based vaccines against *S. pneumoniae*. Therefore, there is a need in the art for alternative vaccines for the prevention of pneumococcal disease.

SUMMARY OF THE INVENTION

The present is an attenuated mutant strain of *Streptococcus pneumoniae* strain, wherein said strain has a mutation in the FtsY gene. In some embodiments, the mutation results in null expression of the FtsY gene. In other embodiments, the FtsY mutant includes a mutation in one or more genes required for autolysis, capsular polysaccharide synthesis, pneumolysin production, competence or mismatch repair. Vaccines and kits containing the attenuated mutant strain and methods for using the vaccine to protect against disease or colonization by a *Streptococcus pneumoniae* strain are also provided.

DETAILED DESCRIPTION OF THE INVENTION

Although deleting virulence genes needed for invasive disease has been used to generate live, attenuated vaccines that elicit reasonable protection in models of pneumococcal disease, the absence of various immunogenic virulence factors that are protective in themselves reduces the potential effectiveness of such vaccines. In this respect, it has now been found that some degree of nasal colonization is needed to protect against subsequent challenge at mucosal sites. Indeed, the results presented herein indicate that although some live vaccines can generate a strong, serotype-independent antibody response, this does not necessarily indicate that the strain is effective at preventing AOM or sinusitis.

The present invention now provides a live, attenuated pneumococcal strain for use in providing protection against ear infections, sinusitis, pneumonia, and sepsis caused by *S. pneumonia*. The live, attenuated pneumococcal strain of the present invention is a mutated strain of *S. pneumonia*, which has a mutation in the gene encoding the signal recognition particle-docking protein FtsY (SEQ ID NO:1), while still being capable of colonizing the mucosa of a subject. In particular, the invention provides a mutated strain derived from a parent *S. pneumoniae* strain, wherein said strain exhibits attenuated pathogenicity compared to the parent strain, and wherein the mutation is in FtsY.

As is conventional in the art, the term "attenuated" refers to a cell, culture, or strain of *Streptococcus* exhibiting a detectable reduction in infectivity or virulence in vitro and/or in vivo as compared to that of the parent strain of *Streptococcus* from which the attenuated cell, culture, or strain is derived. Reduction in virulence encompasses any detectable decrease in any attribute of virulence, including infectivity in vitro and/or in vivo, or any decrease in the severity or rate of progression of any clinical symptom or condition associated with infection.

FtsY refers to the protein provided herein as SEQ ID NO:1 and encoded by SP1244. FtsY is the bacterial homologue of the alpha sub-unit of the eukaryotic Signal Recognition Particle Receptor and has been described for use in generating an immune response in mammals (U.S. Pat. No. 6,214,348). FtsY, and homologues such as Srb (Swissprot accession number P51835), are components of the protein secretory apparatus of bacteria and play an essential role in targeting of proteins to the cytoplasmic membrane. In one embodiment, the FtsY gene is mutated rendering the mutated strain unable to express a functional FtsY protein, i.e., the protein is expressed but is inactive. In another embodiment, the FtsY gene is mutated so that the strain is unable to express FtsY, i.e., null expression.

FtsY mutant strains of the present invention can be prepared by conventional recombinant DNA techniques for gene replacement or gene knockout via homologous recombination. For example, parent S. pneumoniae cells may be transformed or transfected with a vector, such as a plasmid, that includes homologous nucleotide sequences that normally flank, or are located within, the FtsY locus. The vector may also include a selectable marker or a defective FtsY coding sequence inserted between or within the homologous nucleotide sequences (referred to collectively herein as a "replacement construct"). Transformation of a parent cell with the vector is followed by integration of the replacement construct into the S. pneumoniae genome and replacement of the original or "wild-type" FtsY sequence. Thus, the targeted gene is disabled in the transformed parent cell. In one embodiment, insertion of replacement construct results in an inactive, mutant form of the FtsY protein. In other embodiment, insertion of the replacement construct into the FtsY locus results in null expression of FtsY and a FtsY or Fts null mutant strain. Transformed cells may then be screened for those cells that exhibit an attenuated pathogenicity. Transformed cells exhibiting attenuated pathogenicity may then be screened again for those cells that are capable of triggering an immune response in a mammal that protects against S. pneumoniae when administered as a live vaccine.

General techniques of genetic recombination, including vector construction, transformation, selection of transformants, host cell expression, etc., are further described in Maniatis et al, 1989, Molecular Cloning, A Laboratory Manual, Cold Spring Harbor Laboratory Press, Cold Spring Harbor, N.Y.; Ausubel et al., 1989, Current Protocols in Molecular Biology, Greene Publishing Associates & Wiley Interscience, N.Y.; Innis et al. (eds), 1995, PCR Strategies, Academic Press, Inc., San Diego, Calif.; and Erlich (ed), 1992, PCR Technology, Oxford University Press, New York.

As used herein, the term "parent strain" refers to a strain of Streptococcus which exhibits a relatively higher degree of pathogenicity when administered to a subject than an attenuated strain which is derived therefrom by one or more passages in vivo or in vitro and/or one or more attenuation steps. In certain embodiments, the parent strain of S. pneumoniae used in the compositions, cells, vaccines and methods described herein, is TIGR4 referring to a serotype 4 clinical isolate, genome sequence strain; D39 referring to a capsular type 2 clinical isolate; ST162 referring to a serotype 19F strain; P303 referring to a mouse virulent type 6A clinical isolate, or P1121 referring to a type 23F capsule-expressing S. pneumoniae isolate from the human nasopharynx. In one embodiment, the compositions, cells, vaccines and methods described herein can be used with any strain of virulent S. pneumoniae.

Having demonstrated the protective activity of the instant FtsY null mutant, the present invention features mutant cells, compositions, and vaccines for use in treating, preventing or ameliorating a subject against pneumococcal infection or colonization. In this respect, the instant FtsY null mutant is typically provided in the form most suitable for the administration route selected.

In accordance with particular embodiments, the FtsY mutant is used in a vaccine preparation. In general, the vaccine is administered in an immunologically effective amount, which is an amount sufficient to induce a protective immune response in the subject against S. pneumoniae. The live attenuated FtsY null mutant cells described herein are capable of triggering an immune response that protects a mammal against pneumococcal infection or colonization after one or more administrations as a live vaccine. A "protective immune response" refers to any immunological response, either antibody or cell-mediated immunity, or both, occurring in the mammal that either prevents or detectably reduces subsequent infection, or eliminates or detectably reduces the severity, or detectably slows the rate of progression, of one or more clinical symptoms or conditions associated with S. pneumoniae.

The immunogenicity level may be determined experimentally by challenge dose titration study techniques generally known in the art. Such techniques typically include vaccinating a number of subjects with the vaccine at different dosages, and then challenging the subjects with the virulent S. pneumoniae to determine the minimum protective dose.

Factors affecting the preferred dosage regimen may include, for example, the age, weight, sex, diet, activity, and condition of the subject; the route of administration; the efficacy, safety, and duration-of-immunity profiles of the particular vaccine used; whether a delivery system is used; and whether the vaccine is administered as part of a drug and/or vaccine combination. Thus, the dosage actually employed can vary. Determining such dosage adjustments is generally within the skill of those in the art using conventional means.

It is contemplated that the vaccine preparation may be administered to a subject at a single time; or, alternatively, two or more times over days, weeks, months, or years. In some embodiments, the vaccine preparation is administered at least two times. In some such embodiments, for example, the vaccine preparation is administered twice, with the second dose (e.g., the booster) being administered at least about 2 weeks after the first. In some embodiments, the vaccine preparation is administered twice, with the second dose being administered no greater than 8 weeks after the first. In some embodiments, the second dose is administered at from about 2 weeks to about 4 years after the first dose, from about 2 to about 8 weeks after the first dose, or from about 3 to about 4 weeks after the first dose. In some embodiments, the second dose is administered about 4 weeks after the first dose. In the above embodiments, the first and subsequent dosages may vary, such as, for example, in amount and/or form. Often, however, the dosages are the same as to amount and form.

In certain embodiments, the vaccine preparation is administered to a subject that is immunogenically naïve to S. pneumoniae, i.e., the subject has not been vaccinated for S. pneumoniae or exposed to S. pneumoniae. In accordance with this embodiment, the vaccine preparation is administered before the subject recipient is infected with S. pneumoniae. In such embodiments, the vaccine preparation may, for example, be administered to prevent, reduce the risk of, or delay the onset of S. pneumoniae infection or one or more (typically two or more) S. pneumoniae symptoms.

In some embodiments, the vaccine preparation is administered to subjects in a population after a subject in the population has been infected with S. pneumoniae. In such embodiments, the vaccine preparation may, for example, ameliorate, suppress, or eradicate the S. pneumoniae or one or more (typically two or more) S. pneumoniae symptoms in the subjects of the population.

The preferred composition of the vaccine preparation may depend on the method of administration of the vaccine preparation. It is contemplated that the vaccine preparation will include one or more conventional pharmaceutically acceptable carriers, adjuvants, other immune-response enhancers, and/or vehicles (collectively referred to as "excipients"). Such excipients are generally selected to be compatible with the active ingredient(s) in the vaccine preparation. Use of excipients is generally known to those skilled in the art.

The term "pharmaceutically acceptable" is used adjectivally to mean that the modified noun is appropriate for use in a pharmaceutical product. When it is used, for example, to describe an excipient in a pharmaceutical vaccine, it characterizes the excipient as being compatible with the other ingredients of the composition and not disadvantageously deleterious to the intended recipient subject.

The vaccine preparation of the invention can be administered by conventional means, including, for example, mucosal administration, (such as intranasal, oral, intratracheal, and ocular), and parenteral administration (such as, without limitation, subcutaneous or intramuscular administration). The vaccine preparation may also be administered intradermally or transdermally (including, without limitation, via a skin patch or topical administration). Mucosal administration is often particularly advantageous for live attenuated vaccines.

Mucosal vaccine preparations may be, for example, liquid dosage forms, such as pharmaceutically acceptable emulsions, solutions, suspensions, syrups, and elixirs. Excipients suitable for such vaccine preparations include, for example, inert diluents commonly used in the art, such as, water, saline, dextrose, glycerol, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol. Excipients also can comprise various wetting, emulsifying, suspending, flavoring (e.g., sweetening), and/or perfuming agents.

Oral mucosal vaccine preparations also may, for example, be tableted or encapsulated for convenient administration. Such capsules or tablets can contain a controlled-release formulation. In the case of capsules, tablets, and pills, the dosage forms also can comprise buffering agents, such as sodium citrate, or magnesium or calcium carbonate or bicarbonate. Tablets and pills additionally can be prepared with enteric coatings.

"Parenteral administration" includes subcutaneous injections, submucosal injections, intravenous injections, intramuscular injections, intrasternal injections, and infusion. Injectable preparations (e.g., sterile injectable aqueous or oleaginous suspensions) can be formulated according to the known art using suitable excipients, such as vehicles, solvents, dispersing, wetting agents, emulsifying agents, and/or suspending agents. These typically include, for example, water, saline, dextrose, glycerol, ethanol, corn oil, cottonseed oil, peanut oil, sesame oil, benzyl alcohol, benzyl alcohol, 1,3-butanediol, Ringer's solution, isotonic sodium chloride solution, bland fixed oils (e.g., synthetic mono- or diglycerides), fatty acids (e.g., oleic acid), dimethyl acetamide, surfactants (e.g., ionic and non-ionic detergents), propylene glycol, and/or polyethylene glycols. Excipients also may include small amounts of other auxiliary substances, such as pH buffering agents.

The vaccine preparation may include one or more adjuvants that enhance a subject's immune response (which may include an antibody response, cellular response, or both), thereby increasing the effectiveness of the vaccine. The adjuvant(s) may be a substance that has a direct (e.g., cytokine or Bacille Calmette-Guerin (BCG)) or indirect effect (liposomes) on cells of the subject's immune system. Examples of often suitable adjuvants include oils (e.g., mineral oils), metallic salts (e.g., aluminum hydroxide or aluminum phosphate), bacterial components (e.g., bacterial liposaccharides, Freund's adjuvants, and/or MDP), plant components (e.g., Quil A), and/or one or more substances that have a carrier effect (e.g., bentonite, latex particles, liposomes, and/or Quil A). Adjuvants also include, for example, CARBIGEN adjuvant and carbopol. It should be recognized that this invention encompasses both vaccine preparations that include an adjuvant(s), as well as vaccine preparations that do not include any adjuvant.

"Cytokines" used in the compositions, vaccines and methods described herein, refer to small proteins secreted primarily, but not exclusively, by cells of the immune system that promote the proliferation and/or differentiative functions of other cells. Examples of cytokines include interleukins, interferons, hematopoietic colony stimulating factors (CSF), and proinflammatory factors such as tumor necrosis factor (TNF).

It is contemplated that the vaccine preparation may be freeze-dried (or otherwise reduced in liquid volume) for storage, and then reconstituted in a liquid before or at the time of administration. Such reconstitution may be achieved using, for example, vaccine-grade water.

The present invention further includes kits that are suitable for use in performing the methods described above. The kit includes a dosage form of the vaccine described above in an appropriate container and can also optionally include at least one additional component, and, typically, instructions for using the vaccine preparation with the additional component(s). The additional component(s) may, for example, be one or more additional ingredients (such as, for example, one or more of the excipients discussed above) that can be mixed with the vaccine preparation before or during administration. The additional component(s) may alternatively (or additionally) include one or more apparatuses for administering the vaccine to the subject. Such an apparatus may be, for example, a syringe, inhaler, nebulizer, pipette, forceps, or any medically acceptable delivery vehicle. In some embodiments, the apparatus is suitable for subcutaneous administration of the vaccine preparation. In some embodiments, the apparatus is suitable for intranasal administration of the vaccine preparation.

In one embodiment, the vaccines described herein, or the compositions, all which are used in the methods of the invention, establish genetically-modified strains that are unable or less likely to cause disease but can colonize efficiently enough to stimulate protective immune responses. Given that the pneumococci are naturally competent and capable of genetic recombination with the normal host flora, particular embodiments of this invention further include deleting or knocking out the competence or recombination system in the FtsY mutant so that a revertant could not arise. Such a deletion or knock out could include one or more genes of the competence (com) locus (Cheng, et al. (1997) *Mol. Microbiol.* 23:683-92; Whatmore, et al. (1999) *J. Bacteriol.* 181:3144-3154) or mismatch repair (Hex) system (Prudhomee, et al. (1991) *J. Bacteriol.* 173:7196-7203; Claverys, et al. (1984) *Mol. Gen. Genet.* 196:91-96). Alternatively, or in addition to, the attenuated FtsY mutant of the invention can further include gene disruption, gene knock out or gene replacement of genes involved in autolysis, e.g., the lytA gene (Tomasz, et al. (1988) *J. Bacteriol.* 170:5931-5934) so that the FtsY mutant can be grown to stationary phase in a bioreactor. Furthermore, the gene encoding pneumolysin (locus SP1923) can be deleted or replaced with a defective toxoid (e.g., $\Delta 6$, D385N or L460D mutation) to abolish complement activation and/or cytotoxic activity (see Berry, et al. (1995) *Infect. Immun.* 63:1969-1974 and US 2008/0112964). Moreover, certain embodiments feature an unencapsulated (cap-) FtsY mutant with a defect in one or more capsular polysaccharide synthesis genes. By way of illustration, a vaccine the vaccine of the invention can be FtsY-Lyt-Hex- (or com-) toxoid substitution (Δ6, N385 or L460D) cap-.

The compositions, vaccines and kits of this invention are of use in methods for treating, preventing or ameliorating a subject against pneumococcal disease or colonization. Accordingly, the invention provides methods of protecting a subject against infection or colonization by a *S. pneumoniae* strain or protecting a subject against disease caused by *S. pneumoniae* and its various serotypes, by administering to said subject a composition containing an immunologically effective amount of the live, attenuated FtsY null mutant cells described herein. Protecting the subject, refers to preventing a disease, reducing a disease severity, reducing infection, alleviating symptoms associated with a disease, delaying an onset of a disease, or a combination thereof. Diseases that can be prevented by the instant method include, but are not limited to ear infections, sinusitis, pneumonia, and sepsis caused by *S. pneumonia*.

In some embodiments, protection is provided by stimulating an immune response (e.g., cellular and/or humoral responses) in the subject to the FtsY null mutant. In another embodiment, colonization with the live, attenuated pneumococci provided herein, induced increased levels of anti-pneumococcal serum IgG (and mucosal IgA). This serum IgG response accounts in another embodiment, for the observed protection from infection and in another embodiment, offers the possibility of long acting immunity. In one embodiment, the antibody-dependent effects described herein induce protection from infection and in another embodiment, do not require use of a pharmacological adjuvant.

The invention is described in greater detail by the following non-limiting examples.

Example 1

Materials and Methods

Bacterial and Viral Strains and Growth Conditions.

The TIGR4 (serotype 4), D39 (serotype 2), BHN54 (serotype 7F, ST191) (McCullers, et al. (2010) *J. Infect. Dis.* 202: 1287-95) and BHN97 (serotype 19F, ST425, also known as SME33) (McCullers, et al. (2007) *PLoS Pathog.* 3:e28; McCullers, et al. (2010) supra) parent and mutant pneumococcal strains were grown overnight at 37° C. in a 5% $CO_2$-humidified incubator after being inoculated onto tryptic soy agar (TSA) plates supplemented with 3% sheep blood. Strains were then inoculated directly into semisynthetic liquid culture (CY broth) and grown to log phase before being administered to mice. The St. Jude strain of mouse adapted influenza virus A/Puerto Rico/8/34 (H1N1; PR8), generated by reverse genetics (McAuley, et al. (2007) *Cell Host Microbe* 2:240-9), was grown in Madin-Darby canine kidney (MDCK) cells.

Generation of Mutants.

Stable mutations in caxP (SEQ ID NO:2)(encoded by SP1551) and ftsY (SEQ ID NO:1) (encoded by SP1244) were generated by PCR SOEing according to standard methods (Horton (1995) *Mol. Biotechnol.* 3:93-99). Briefly, the coding region for caxP or ftsY was replaced with an erythromycin-resistance cassette by using homologous recombination. Transformants were selected on TSA plates supplemented with 3% sheep blood and erythromycin (1 μg/mL) after an overnight incubation at 37° C. in a 5% $CO_2$ humidified incubator. The ftsY- and caxP-strains in both backgrounds render the pneumococci avirulent, with at least a 3-log difference in $LD_{50}$ compared to the parental strains. At the highest dosages of $10^8$ CFUs, survival greater than 90% was observed for all live-attenuated strains.

Vaccination Protocol.

Seven week old BALB/cJ mice were vaccinated with $10^5$ colony-forming units (CFUs) of the respective mutant strains in a volume of 25 μL PBS intranasally. Mock-treated animals received PBS carrier alone. PCV7 (Wyeth Pharmaceuticals Inc.), PCV13 (Wyeth Pharmaceuticals Inc.), and PPV23 (Merck and Co., Inc.) vaccines were commercially acquired and were diluted in saline 1:10 and 100 μL was administered by intraperitoneal injection. After 4 weeks, mice were boosted twice at 2 week intervals. Serum was collected one week following the final boost and mice were challenged two weeks after the final boost. Vaccination regimens were the same for all experimental conditions with all mice receiving 3 total vaccinations.

Mouse Challenge.

To study acute otitis media (AOM), groups of mice (n=10-31) were challenged intranasally with $10^5$ CFUs of BHN54 or BHN97 in 100 μL phosphate-buffered saline (PBS) as described (McCullers, et al. (2007) supra). To model invasive disease, mice were challenged intranasally with $10^7$ CFUs of TIGR4 or D39 in 25 μL PBS. The D39, BHN54, and BHN97 challenge strains had been engineered to express luciferase (Francis, et al. (2001) *Infect. Immun.* 69:3350-3358). In experiments involving influenza, PR8 was given intranasally in a volume of 100 μl of sterile PBS at a dose of 30 $TCID_{50}$.

Monitoring Disease.

The mice were monitored for AOM and sinusitis twice daily starting 6 hours post-challenge and continuing until 72 hours post-challenge. The mice were also monitored for weight loss over the entire challenge period. To monitor progression of disease, mice were anesthetized with 2.5% inhaled isoflurane before in vivo images of their left and right sides were taken. During experiments modeling invasive disease, the bacterial burden in the bloodstream was measured by counting the CFUs formed by serial dilutions of blood collected from the mice. Mice were monitored daily for signs of infection.

Histology.

Mice were euthanized at 24 or 72 hours post-infection, and immediately perfused with 10% buffered formalin (Thermo Scientific, Kalamazoo, Mich.) via the left cardiac ventricle. Additional formalin fixative was gently infused by syringe into the nasal passages and then the intact heads were post-fixed by immersion in 10% buffered formalin for an additional 48 hours before being decalcified in formic acid (TBD-2 Decalcifier, Thermo Scientific, Kalamazoo, Mich.). Multiple coronal sections of the head at the level of the ears and nasal passages were trimmed and embedded in paraffin, and five μm-thick sections were prepared and stained with hematoxylin and eosin for evaluation of inflammatory and degenerative lesions in the nasal passages, sinuses, and middle ear.

ELISAs.

To measure serum titers against different pneumococcal serotypes, bacterial strains were grown in C+Y broth until their optical densities at 620 nm were 0.5. Strains were diluted serially in 0.1M carbonate buffer (pH 9.6) and transferred to 96-well ELISA plates (NUNC). The plates were spun at 2000 g for 10 minutes before the supernatant was removed. The plates were dried under a vent hood for 1 hour before unbound antibody sites were blocked in 10% FBS for 2 hours. Mouse serum from vaccinated animals was serially diluted in 10% FBS before it was added to the wells. The plates were then washed 3 times with wash buffer (1% TWEEN 20, 1 mM Tris, 154 mM NaCl), incubated with primary antibody for 1 hour, washed 5 times, and incubated with alkaline phosphatase (AP)-conjugated anti-mouse IgG (Southern Biotech) (1:2000) for 1 hour. The plates were washed 5 times and then incubated 20 minutes in AP-yellow one component microwell substrate (Sigma) before measurements of their optical densities at 405 nm were taken in a SPECTRAMAX 340 plate reader (Molecular Devices). To measure serum antibody levels against specific proteins, recombinant proteins were all expressed in E. coli and purified over a $Ni^{++}$ column. The proteins utilized were rCbpA (amino acids 175-443 of SP2190 from TIGR4), rPspA (amino acids 1-302 from strain Rx1), and PLY (amino acids 1-472 from D39). One hundred nanograms of protein were used to coat the plates.

CD4 Depletions.

Mice were depleted of $CD4^+$ T-cells 48 hours prior to vaccination, the day of vaccination, and hours post-vaccination by injection of CD4-specific antibodies as described (Wanzeck, et al. (2011) *Am. J. Respir. Crit. Care Med.* 183: 767-773). Briefly, mice were injected with ascites fluid containing the CD4-specific monoclonal antibody (MAb) GK1.5 commencing 3 days before infection and continuing at 2 day intervals thereafter as described (Riberdy, et al. (1999) *J. Virol.* 73:1453-59). The efficacy of the protocol was checked at the time of sampling, with flow cytometric analysis (anti-CD4-PE) showing <1% of the respective population remaining to confirm that the depletions were effective.

Immunoglobulin Subtyping.

Mouse serum from vaccinated and mock-treated animals was collected 96 hours post-challenge as a terminal bleed. The serum was subtyped using the MILLIPORE Mouse Immunoglobulin Isotyping Kit according to the manufacturer's instructions.

Statistical Analyses.

Comparison of survival between groups of mice was done with the Log Rank chi-squared test on the Kaplan-Meier survival data. Comparison of antibody titers and weight loss was done using analysis of variance (ANOVA). Comparison of proportions of otitis media, sinusitis, and pneumonia were done with the Chi-squared test with corrections for multiple comparisons. A p-value of <0.05 was considered significant for these comparisons. SIGMASTAT for WINDOWS (SysStat Software, Inc., V 3.11) was used for all statistical analyses.

Example 2

Live, Attenuated Vaccines Induce Potent Antibody Responses

For the live vaccine candidates, the serotype 2 strain D39 and serotype 19F strain BHN97 were used. D39 is normally an invasive strain that causes pneumonia and sepsis (Kim, et al. (2012) *Vaccine* 30:2008-2019), whereas the 19F strain normally causes sinusitis/purulent rhinitis and AOM (Crowley, et al. (2004) *FEMS Microbiol. Lett.* 234:315-24). In each of these backgrounds, two separate mutants were generated using deletions targeting ftsY and caxP. The vaccines utilized and their relevant characteristics are detailed in Table 1.

TABLE 1

| Vaccine | Serotype(s) | Relevant characteristics |
| --- | --- | --- |
| D39ΔftsY | 2 | Live, attenuated, colonizing strain, heterologous challenge [1] |
| D39ΔcaxP | 2 | Live, attenuated, non-colonizing strain, heterologous challenge |
| BHN97ΔftsY | 19F | Live, attenuated, colonizing strain, homologous challenge |
| BHN97ΔcaxP | 19F | Live, attenuated, non- colonizing strain, homologous challenge |
| PCV7 | 4, 6B, 9V, 14, 18C, 19F, and 23F | Multivalent, conjugated polysaccharide vaccine, homologous challenge |
| PCV13 | 1, 3, 4, 5, 6A, 6B, 7F, 9V, 14, 18C, 19A, 19F, and 23F | Multivalent, conjugated polysaccharide vaccine, homologous challenge |
| PPV23 | 1, 2, 3, 4, 5, 6B, 7F, 8, 9N, 9V, 10A, 11A, 12F, 14, 15B, 17F, 18C, 19A, 19F, 20, 22F, 23F and 33F | Multivalent polysaccharide vaccine, homologous challenge |
| Mock | None | Carrier only as baseline control |

[1] Vaccination is homologous or heterologous to the serotype 19F, AOM- and sinusitis-causing challenge strain.

Deletion of caxP in both strain backgrounds resulted in an inability to colonize the nasopharynx within 24 hours of inoculation. The ftsY mutants were able to colonize for longer but with significantly reduced titers compared to the parental strain. The BHN97 ΔftsY strain had the longest colonization duration of any of the mutants, being cleared after 7 days as opposed to 3 days or less for the other strains. The deletion of either caxP or ftsY had no effect on the expression of the antigenic virulence proteins pneumolysin, CbpA, or PspA. Deletion of caxP has previously been shown to completely attenuate pneumococcus, a pattern consistent with the findings herein of complete clearance within 24 hours. Deletion of ftsY rendered the pneumococcus highly attenuated in D39x background, with no translocation into the bloodstream or mortality observed with this strain compared to the parental D39x. While the BHN97 strain does not typically result in mortality in mice, deletion of ftsY resulted in marked decreases in both lung and sinus inflammation compared to the parental strain. These data indicate that these strains are sufficiently defective in both mucosal and invasive disease to warrant their use as live vaccine candidates.

Vaccine combinations that included the commercially available 7-valent conjugate (PCV7) and 23-valent polysaccharide (PPV23) vaccines were analyzed for their ability to induce anti-pneumococcal antibodies as measured by ELISA. All four live vaccines generated high levels of antibodies reactive against pneumococcus in a serotype-independent manner. Detectable quantities of antibodies above baseline were not observed from the PPV23 vaccine, but a robust response against serotype 4 was seen in the PCV7 vaccinated animals and a modest but statistically elevated titer was seen against serotype 19F. The anti-serotype 4 response was reduced when an unencapsulated version of TIGR4 (T4R) was tested against PCV7 sera, while the titers induced by the live vaccines were unchanged. The BHN97ΔftsY vaccine elicited significantly higher titers of antibodies against all strains compared to all other vaccines, independent of the capsular serotype of the test strain. Thia may be in part due to the prolonged colonization phenotype observed with this vaccine strain compared with the others. It was concluded that the live, attenuated vaccine BHN97ΔftsY was significantly more immunogenic than comparator vaccines in mice, and that immune responses to this strain were largely capsule-independent and were not serotype specific.

Example 3

Relative Efficacy of Live Vaccines for Mucosal Protection

Following vaccination, mice were challenged with a version of BHN97 which expresses luciferase (Smith, et al. (2007) *Comp. Med.* 57:82-89; McCullers, et al. (2007) supra) and were followed twice daily by bioluminescent imaging to assess vaccine protection against AOM and sinusitis. BHN97 caused AOM in approximately 80% of naïve animals within 24 hours of inoculation. Sinusitis developed at the same time or shortly after the otitis infection in most mice, typically peaking within 72 hours after challenge. The incidence of otitis media was significantly ($P<0.05$ compared to mock) lower in the PCV7-vaccinated and BHN97ΔftsY-vaccinated mice. The PPV23 and other live, attenuated vaccines did not confer any significant degree of protection against otitis despite inducing high amounts of anti-pneumococcal antibodies. Only the BHN97ΔftsY vaccine significantly decreased the incidence of sinusitis ($p<0.05$). Measurement of the total luminescence of the ears and sinuses at 24 and 72 hours, respectively, confirmed the protection engendered by the PCV and BHN97ΔftsY vaccines. Weight loss was also monitored in the mice as a measure of the relative morbidity caused by the infection. Interestingly, PCV7 and all the live vaccines conferred a significant decrease in the amount of weight loss 72 hours after infection ($p<0.01$). The BHN97ΔftsY vaccine also elicited antibody responses against pneumolysin, CbpA, and PspA at significantly higher levels than intranasally administered heat-killed BNH97. Additional analysis of the BHN97ΔftsY vaccine was therefore conducted.

Example 4

Live Vaccine Elicits Serotype-Independent Protection Against Otitis Media

It was subsequently determine whether heterologous protection was conferred by the BHN97ΔftsY vaccine using a serotype 7F strain of pneumococcus (BHN54) that causes AOM in approximately 50% of infected animals. Because serotype 7F is included in PCV13, that vaccine was used as a control. The BHN97ΔftsY-vaccinated animals had a significantly lower incidence of AOM and reduced luminescent signals in the ears than did the mock-vaccinated animals ($p<0.05$). Heterologous protection by BHN97ΔftsY vaccination was indistinguishable from the homologous protection afforded by the PCV13 vaccine. The BHN97ΔftsY-vaccinated group had significantly less morbidity (measured by percentage of weight loss) than did the mock- and PCV13-vaccinated groups ($p<0.05$) 24 hours after infection. It was concluded that the BHN97ΔftsY vaccine conferred effective serotype-independent protection against AOM.

Example 5

A Live, Attenuated Vaccine Protects Against Heterologous Lethal Challenges

To determine the protection by the live vaccine in invasive disease, the efficacy of BHN97ΔftsY against lethal, heterologous pneumococcal challenges was determined. Mice were challenged with D39 (type 2) or TIGR4 and followed for mortality. Both challenge strains are heterologous to the BHN97ΔftsY vaccine, while serotype 4, but not serotype 2, is contained in the control vaccine, PCV13. Vaccination with BHN97ΔftsY resulted in significant protection against sepsis and death for both challenges compared to mock vaccination. Protection was better against D39, which causes pneumonia with secondary sepsis, than against TIGR4, which causes primarily bacteremia, evidenced by the fact the TIGR4 strain resulted in bacteremia within 24 hours whereas D39x mice became bacteremic at later time points, typically 48-72 hours post-infection. The BHN97ΔftsY vaccine resulted in significantly decreased bacterial titers in the blood following infection for both the TIGR4 and D39x challenge. The PCV13 vaccine elicited excellent protection against the homologous TIGR4 challenge but provided no benefit against the heterologous D39 infection.

Passive protection studies were subsequently carried out to determine whether the heterologous protection was antibody-mediated. Mice were given a single injection of either mock, PCV13, or BHN97ΔftsY serum one hour prior to infection with D39x. The BHN97ΔftsY serum was able to confer protection against subsequent D39x challenge. It was concluded that BHN97ΔftsY protects against heterologous invasive disease and this protection is primarily antibody-mediated.

Example 6

A Live, Attenuated Vaccine Protects Against Secondary Bacterial Pneumonia

It is increasingly recognized that prior influenza infection is a major predisposing factor to bacterial pneumonia and invasive pneumococcal disease (McCullers (2006) *PLoS Pathog.* 19:571-82). Therefore, this synergism was modeled by administering a sublethal dose of influenza virus that caused a mild pulmonary infection but no significant decrease in weight 7 days post-infection. At post-infection day 7, mice were challenged with BHN97 and monitored for the development of disease by bioluminescent imaging. Within 24 hours of pneumococcal challenge, 90% of the mock-vaccinated animals had developed pneumonia. However, the PCV13 vaccine significantly ($P<0.05$) reduced the incidence of pneumonia to 30%, and the BHN97ΔftsY vaccine completely prevented the development of pneumonia). In this experimental model, the incidence of viral-associated AOM in the mock- and PCV13-vaccinated mice was similar; however, the BHN97ΔftsY vaccine reduced otitis incidence ($p<0.05$). BHN97ΔftsY was also the most effective vaccine of the three in terms of preventing weight loss at 24, 48, and 72 hours after infection. Both the PCV13 and BHN97ΔftsY vaccines prevented mortality from homologous challenge in this synergistic model of secondary bacterial infection. It was concluded that the effectiveness of the BHN97ΔftsY vaccine is retained in the setting of prior viral infection, despite the diminished ability of the host to mount an appropriate immune response (McCullers & Huber (2012) *Human Vaccine Immunother.* 8:34-44; McCullers (2011) *Antivir. Ther.* 16:123-35).

Example 7

A Live, Attenuated Vaccine Elicits a Distinct Antibody Response that is Dependent on CD4+ T-Cells To address the role of antibody isotypes in protection and begin to understand the mechanism of enhanced protection from the BHN97ΔftsY vaccine, the levels of total immunoglobulin isotypes were measured in mouse serum 96 hours following challenge to measure total serum antibody. Since it is known that conjugate vaccine responses are dependent on CD4+ T-cell help, in some experiments CD4+ T-cells were depleted from groups of mice at the time of vaccination to abrogate these cells' contribution to development of immunity. The antibody response to PCV13 was dominated by IgG1; significant levels of IgM, IgA, or other IgG isotypes were not seen. However, this response was abrogated in the absence of CD4+ T-cells. In contrast, the BHN97ΔftsY vaccine did not significantly induce IgG1 production in vaccinated animals. Immune responses to BHN97ΔftsY were shifted toward the production of IgG2a, IgG2b, and IgA. Interestingly, each of these responses required the presence of CD4+ T-cells during vaccination. No significant differences were observed in any of the animals in terms of IgM or IgG3 levels.

This isotype switch to the IgG2 and IgA pattern correlated with the degree of protection against AOM, indicating that the response elicited to the live vaccine is the more optimal antibody isotype distribution to engender protection against AOM. Therefore, the relative contribution of CD4+ T-cells in the development of the mucosal protection that is conferred by the BHN97ΔftsY vaccine was investigated. Mice that had been depleted of CD4+ T-cells during vaccination with either PCV13 or BHN97ΔftsY had higher incidences of AOM than did mice with intact CD4+ T-cells during vaccination, indicating that CD4+ T-cell help is required for an effective response from these vaccines. Depletion of CD4+ T-cells at the time of challenge did not have a statistically significant effect on protection, though modest increases in the incidence and severity of AOM were observed suggesting these cells may also play a direct role in protection. It was concluded that CD4+ T-cell dependent isotype switching is required for protection from AOM when mediated by the live, attenuated pneumococcal vaccine BHN97ΔftsY.

What is claimed is:

1. An attenuated mutant strain of *Streptococcus pneumoniae* comprising a mutation in the FtsY gene, and further comprising a mutation in one or more genes of the competence locus or mismatch repair system, one more genes required for autolysis, the pneumolysin locus, one or more genes required for caspsular polysaccharide synthesis, or a combination thereof.

2. A vaccine comprising a pharmaceutically acceptable excipient and an immunologically effective amount of the attenuated mutant strain of claim 1.

3. A kit comprising the attenuated mutant strain of claim 1.

4. The kit of claim 3, further comprising an excipient.

5. A method of protecting against disease or colonization by a *Streptococcus pneumoniae* strain, comprising administering to a subject in need thereof the vaccine of claim 2, thereby protecting the subject against disease or colonization by a *Streptococcus pneumoniae* strain.

6. The method of claim 5, wherein protecting the subject against disease or colonization by a *Streptococcus pneumoniae* strain comprises preventing, reducing the severity, alleviating symptoms, or delaying onset of ear infections, sinusitis, pneumonia, and sepsis caused by *S. pneumonia*.

* * * * *

UNITED STATES PATENT AND TRADEMARK OFFICE
CERTIFICATE OF CORRECTION

| | | |
|---|---|---|
| PATENT NO. | : 9,265,819 B2 | Page 1 of 1 |
| APPLICATION NO. | : 14/345988 | |
| DATED | : February 23, 2016 | |
| INVENTOR(S) | : Jason W. Rosch | |

It is certified that error appears in the above-identified patent and that said Letters Patent is hereby corrected as shown below:

In the Claims

Column 19, line 55, claim 1, delete "one more"
Column 19, line 55, claim 1, insert --one or more--

Signed and Sealed this
Twenty-fourth Day of May, 2016

Michelle K. Lee
*Director of the United States Patent and Trademark Office*

SEQUENCE LISTING

```
<160> NUMBER OF SEQ ID NOS: 2

<210> SEQ ID NO 1
<211> LENGTH: 425
<212> TYPE: PRT
<213> ORGANISM: Streptococcus pneumoniae

<400> SEQUENCE: 1

Met Gly Leu Phe Asp Arg Leu Phe Gly Lys Lys Glu Glu Pro Lys Ile
1               5                   10                  15

Glu Glu Val Val Lys Glu Ala Leu Glu Asn Leu Asp Leu Ser Glu Asp
            20                  25                  30

Val Asp Pro Thr Phe Thr Glu Val Glu Val Ser Gln Glu Glu Ala
        35                  40                  45

Glu Val Glu Ile Val Glu Gln Ala Val Phe Gln Glu Glu Ile Gln
    50                  55                  60

Asp Thr Val Glu Glu Ser Leu Asp Leu Glu Pro Val Val Glu Val Ser
65                  70                  75                  80

Gln Lys Glu Val Glu Glu Phe Pro His Ser Glu Glu Gly Asn Thr Glu
                85                  90                  95

Phe Leu Glu Thr Ile Glu Glu Asn Asn Ser Glu Val Leu Glu Pro Glu
                100                 105                 110

Arg Pro Gln Ala Glu Glu Thr Val Gln Glu Lys Tyr Asp Arg Ser Leu
            115                 120                 125

Lys Lys Thr Arg Thr Gly Phe Gly Ala Arg Leu Asn Ala Phe Phe Ala
    130                 135                 140

Asn Phe Arg Ser Val Asp Glu Glu Phe Phe Glu Glu Leu Glu Glu Leu
145                 150                 155                 160

Leu Ile Met Ser Asp Val Gly Val Gln Val Ala Ser Asn Leu Thr Glu
                165                 170                 175

Glu Leu Arg Tyr Glu Ala Lys Leu Glu Asn Ala Lys Lys Pro Asp Ala
            180                 185                 190

Leu Arg Arg Val Ile Ile Glu Lys Leu Val Glu Leu Tyr Glu Lys Asp
        195                 200                 205

Gly Ser Tyr Asp Glu Ser Ile His Phe Gln Asp Asn Leu Thr Val Met
    210                 215                 220

Leu Phe Val Gly Val Asn Gly Val Gly Lys Thr Thr Ser Ile Gly Lys
225                 230                 235                 240

Leu Ala His Arg Tyr Lys Gln Ala Gly Lys Lys Val Met Leu Val Ala
```

```
                    245                 250                 255
Ala Asp Thr Phe Arg Ala Gly Ala Val Ala Gln Leu Ala Glu Trp Gly
                260                 265                 270

Arg Arg Val Asp Val Pro Val Val Thr Gly Pro Glu Lys Ala Asp Pro
            275                 280                 285

Ala Ser Val Val Phe Asp Gly Met Glu Arg Ala Val Ala Glu Gly Ile
        290                 295                 300

Asp Ile Leu Met Ile Asp Thr Ala Gly Arg Leu Gln Asn Lys Asp Asn
305                 310                 315                 320

Leu Met Ala Glu Leu Glu Lys Ile Gly Arg Ile Ile Lys Arg Val Val
                325                 330                 335

Pro Glu Ala Pro His Glu Thr Phe Leu Ala Leu Asp Ala Ser Thr Gly
            340                 345                 350

Gln Asn Ala Leu Val Gln Ala Lys Glu Phe Ser Lys Ile Thr Pro Leu
        355                 360                 365

Thr Gly Ile Val Leu Thr Lys Ile Asp Gly Thr Ala Arg Gly Gly Val
370                 375                 380

Val Leu Ala Ile Arg Glu Glu Leu Asn Ile Pro Val Lys Leu Ile Gly
385                 390                 395                 400

Phe Gly Glu Lys Ile Asp Asp Ile Gly Glu Phe Asn Ser Glu Asn Phe
                405                 410                 415

Met Lys Gly Leu Leu Glu Gly Leu Ile
            420                 425

<210> SEQ ID NO 2
<211> LENGTH: 914
<212> TYPE: PRT
<213> ORGANISM: Streptococcus pneumoniae

<400> SEQUENCE: 2

Met Thr Glu Arg Glu Ser Val Leu His Thr Met Ser Arg Arg His
1               5                   10                  15

Met Ser Lys Glu Gln Lys Arg Gln Ala Phe Tyr Thr Gln Ser Pro Glu
                20                  25                  30

Glu Val Leu Gln Ala Val Asp Ala Thr Glu Gln Gly Leu Ser Ser Ser
            35                  40                  45

Glu Ala Glu Lys Arg Leu Ala Glu Phe Gly His Asn Glu Leu Glu Glu
        50                  55                  60

Gly Glu Lys Arg Ser Ile Leu Val Lys Phe Ile Glu Gln Phe Lys Asp
65                  70                  75                  80

Leu Met Ile Ile Ile Leu Val Ala Ala Ala Ile Leu Ser Val Val Thr
                85                  90                  95

Ser Gly Gly Glu Asp Ile Ala Asp Ala Ile Ile Leu Ala Val Val
            100                 105                 110

Ile Ile Asn Ala Ala Phe Gly Val Tyr Gln Glu Gly Lys Ala Glu Glu
        115                 120                 125

Ala Ile Glu Ala Leu Lys Ser Met Ser Ser Pro Val Ala Arg Val Leu
130                 135                 140

Arg Asp Gly His Met Ala Glu Ile Asp Ser Lys Glu Leu Val Pro Gly
145                 150                 155                 160

Asp Ile Val Ala Leu Glu Ala Gly Asp Val Val Pro Ala Asp Leu Arg
                165                 170                 175

Leu Ile Glu Ala Asn Ser Leu Lys Ile Glu Glu Ala Ala Leu Thr Gly
            180                 185                 190
```

```
Glu Ser Val Pro Val Glu Lys Asp Leu Ser Val Glu Leu Ala Thr Asp
        195                 200                 205

Ala Gly Ile Gly Asp Arg Val Asn Met Ala Phe Gln Asn Ser Asn Val
    210                 215                 220

Thr Tyr Gly Arg Gly Met Gly Val Val Asn Thr Gly Met Tyr Thr
225             230                 235                 240

Glu Val Gly His Ile Ala Gly Met Leu Gln Asp Ala Asp Glu Thr Asp
                245                 250                 255

Thr Pro Leu Lys Gln Asn Leu Asn Asn Leu Ser Lys Val Leu Thr Tyr
            260                 265                 270

Ala Ile Leu Val Ile Ala Leu Val Thr Phe Val Val Gly Val Phe Ile
        275                 280                 285

Gln Gly Lys Asn Pro Leu Gly Glu Leu Leu Thr Ser Val Ala Leu Ala
    290                 295                 300

Val Ala Ala Ile Pro Glu Gly Leu Pro Ala Ile Val Thr Ile Val Leu
305                 310                 315                 320

Ser Leu Gly Thr Gln Val Leu Ala Lys Arg His Ser Ile Val Arg Lys
                325                 330                 335

Leu Pro Ala Val Glu Thr Leu Gly Ser Thr Glu Ile Ile Ala Ser Asp
            340                 345                 350

Lys Thr Gly Thr Leu Thr Met Asn Lys Met Thr Val Glu Lys Val Phe
        355                 360                 365

Tyr Asp Ala Val Leu His Asp Ser Ala Asp Asp Ile Glu Leu Gly Leu
    370                 375                 380

Glu Met Pro Leu Leu Arg Ser Val Val Leu Ala Asn Asp Thr Lys Ile
385                 390                 395                 400

Asp Val Glu Gly Asn Leu Ile Gly Asp Pro Thr Glu Thr Ala Phe Ile
                405                 410                 415

Gln Tyr Ala Leu Asp Lys Gly Tyr Asp Val Lys Gly Phe Leu Glu Lys
            420                 425                 430

Tyr Pro Arg Val Ala Glu Leu Pro Phe Asp Ser Asp Arg Lys Leu Met
        435                 440                 445

Ser Thr Val His Pro Leu Pro Asp Gly Arg Phe Leu Val Ala Val Lys
450                 455                 460

Gly Ala Pro Asp Gln Leu Leu Lys Arg Cys Leu Leu Arg Asp Lys Ala
465                 470                 475                 480

Gly Asp Ile Ala Pro Ile Asp Glu Lys Val Thr Asn Leu Ile Arg Thr
                485                 490                 495

Asn Asn Ser Glu Met Ala His Gln Ala Leu Arg Val Leu Ala Gly Ala
            500                 505                 510

Tyr Lys Ile Ile Asp Ser Ile Pro Glu Asn Leu Thr Ser Glu Glu Leu
        515                 520                 525

Glu Asn Asp Leu Ile Phe Thr Gly Leu Ile Gly Met Ile Asp Pro Glu
    530                 535                 540

Arg Pro Glu Ala Ala Glu Ala Val Arg Val Ala Lys Glu Ala Gly Ile
545                 550                 555                 560

Arg Pro Ile Met Ile Thr Gly Asp His Gln Asp Thr Ala Glu Ala Ile
                565                 570                 575

Ala Lys Arg Leu Gly Ile Ile Asp Ala Asn Asp Thr Glu Gly His Val
            580                 585                 590

Leu Thr Gly Ala Glu Leu Asn Glu Leu Ser Asp Glu Glu Phe Glu Lys
        595                 600                 605

Val Val Gly Gln Tyr Ser Val Tyr Ala Arg Val Ser Pro Glu His Lys
```

```
                    610                 615                 620
Val Arg Ile Val Lys Ala Trp Gln Lys Gln Gly Lys Val Val Ala Met
625                 630                 635                 640

Thr Gly Asp Gly Val Asn Asp Ala Pro Ala Leu Lys Thr Ala Asp Ile
                    645                 650                 655

Gly Ile Gly Met Gly Ile Thr Gly Thr Glu Val Ser Lys Gly Ala Ser
                    660                 665                 670

Asp Met Ile Leu Ala Asp Asp Asn Phe Ala Thr Ile Ile Val Ala Val
                675                 680                 685

Glu Gly Arg Lys Val Phe Ser Asn Ile Gln Lys Thr Ile Gln Tyr
        690                 695                 700

Leu Leu Ser Ala Asn Thr Ala Glu Val Leu Thr Ile Phe Leu Ser Thr
705                 710                 715                 720

Leu Phe Gly Trp Asp Val Leu Gln Pro Val His Leu Leu Trp Ile Asn
                725                 730                 735

Leu Val Thr Asp Thr Phe Pro Ala Ile Ala Leu Gly Val Glu Pro Ala
                740                 745                 750

Glu Pro Gly Val Met Asn His Lys Pro Arg Gly Arg Lys Ala Ser Phe
            755                 760                 765

Phe Ser Gly Gly Val Leu Ser Ser Ile Ile Tyr Gln Gly Val Leu Gln
        770                 775                 780

Ala Ala Leu Val Met Ser Val Tyr Gly Leu Ala Ile Ala Tyr Pro Val
785                 790                 795                 800

His Val Gly Asp Asn His Ala Ile His Ala Asp Ala Leu Thr Met Ala
                805                 810                 815

Phe Ala Thr Leu Gly Leu Ile Gln Leu Phe His Ala Tyr Asn Val Lys
                820                 825                 830

Ser Val Tyr Gln Ser Ile Leu Thr Val Gly Pro Phe Lys Ser Lys Thr
            835                 840                 845

Phe Asn Trp Ser Ile Leu Val Ser Phe Ile Leu Leu Met Ala Thr Ile
        850                 855                 860

Val Val Glu Pro Leu Glu Gly Ile Phe His Val Thr Lys Leu Asp Leu
865                 870                 875                 880

Ser Gln Trp Gly Ile Val Met Ala Gly Ser Phe Ser Met Ile Ile Ile
                885                 890                 895

Val Glu Ile Val Lys Phe Ile Gln Arg Lys Leu Gly Phe Asp Lys Asn
            900                 905                 910

Ala Ile
```